(12) United States Patent
Grodzki (10) Patent No.: US 10,101,421 B2
(45) Date of Patent: Oct. 16, 2018

(54) MAGNETIC RESONANCE APPARATUS, AND METHOD AND CONTROL DEVICE THEREFOR

(71) Applicant: Siemens Aktiengesellschaft, Munich (DE)

(72) Inventor: David Grodzki, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1070 days.

(21) Appl. No.: 14/454,079

(22) Filed: Aug. 7, 2014

(65) Prior Publication Data

US 2015/0042333 A1 Feb. 12, 2015

(30) Foreign Application Priority Data

Aug. 7, 2013 (DE) .......................... 10 2013 215 549

(51) Int. Cl.
| | | |
|---|---|---|
| *G01R 33/385* | (2006.01) | |
| *G01R 33/28* | (2006.01) | |
| *G01R 33/38* | (2006.01) | |
| *G01R 33/54* | (2006.01) | |
| *A61B 5/055* | (2006.01) | |

(52) U.S. Cl.
CPC ....... *G01R 33/3854* (2013.01); *G01R 33/288* (2013.01); *G01R 33/3804* (2013.01); *G01R 33/543* (2013.01); *A61B 5/055* (2013.01); *A61B 2560/0242* (2013.01); *A61B 2562/0204* (2013.01)

(58) Field of Classification Search
CPC .............. G01R 33/288; G01R 33/3804; G01R 33/543; G01R 33/3854; A61B 5/055; A61B 2560/0242; A61B 2562/0204
See application file for complete search history.

(56) References Cited

U.S. PATENT DOCUMENTS

| | | | | |
|---|---|---|---|---|
| 5,436,564 A * | 7/1995 | Kreger | ................. | A61B 5/0424 128/901 |
| 5,545,991 A * | 8/1996 | Nauerth | ............. | G01R 33/4818 324/307 |
| 5,661,399 A * | 8/1997 | Sellers | ............... | G01R 33/3854 324/318 |
| 5,990,680 A * | 11/1999 | Mansfield | .......... | G01R 33/3854 324/318 |
| 6,288,540 B1 * | 9/2001 | Chen | ................ | G01R 33/56341 324/300 |
| 6,407,548 B1 | 6/2002 | Dietz | | |
| 6,954,666 B2 * | 10/2005 | Bechtold | ................ | A61B 5/055 600/410 |
| 7,112,965 B2 * | 9/2006 | Scheffler | ............ | G01R 33/4806 324/309 |
| 8,432,165 B2 * | 4/2013 | Weiger Senften | .......................... | G01R 33/4616 324/307 |

(Continued)

*Primary Examiner* — Dixomara Vargas
(74) *Attorney, Agent, or Firm* — Schiff Hardin LLP (57) ABSTRACT

In a method to control a magnetic resonance apparatus, a control device, a magnetic resonance apparatus, and an electronically readable data storage medium, a reduction and/or limitation and/or monitoring of the noise volume of the magnetic resonance apparatus is enabled by a noise volume-reduced operating mode of the magnetic resonance apparatus being activated depending on at least one predeterminable event.

12 Claims, 2 Drawing Sheets

(56) References Cited

U.S. PATENT DOCUMENTS

| | | | | |
|---|---|---|---|---|
| 9,778,339 B2 * | 10/2017 | Grodzki | ............... | G01R 33/546 |
| 2003/0212328 A1 * | 11/2003 | Bechtold | ................ | A61B 5/055 |
| | | | | 600/437 |
| 2012/0074938 A1 | 3/2012 | Grodzki et al. | | |
| 2014/0232396 A1 * | 8/2014 | Grodzki | ............... | G01R 33/543 |
| | | | | 324/309 |
| 2015/0108981 A1 * | 4/2015 | Grodzki | ............. | G01R 33/3671 |
| | | | | 324/318 |

* cited by examiner

FIG 2

MAGNETIC RESONANCE APPARATUS, AND METHOD AND CONTROL DEVICE THEREFOR

BACKGROUND OF THE INVENTION

Field of the Invention

The present invention concerns a method to control a magnetic resonance apparatus, as well as a control device for controlling magnetic resonance apparatus in accordance with the method, a magnetic resonance apparatus embodying such a control device, and a non-transitory computer-readable data storage medium encoded with programming instructions to cause such a control device to implement the method.

Description of the Prior Art

During a magnetic resonance examination, magnetic field gradients are required for imaging. These are generated with gradient coils. In most magnetic resonance sequences, the polarity and the strength of the gradients must be modified in extremely short time intervals. During the switching process, minimal distortions and/or expansions of the magnet coil occur, causing loud noises to be created and making hearing protection for the patient necessary. Loud noises also can be created in the transmission or reception coils upon switching between the transmission mode and the reception mode. Furthermore, the magnet cooling of the magnetic resonance apparatus causes a periodic noise. Given conventional imaging sequences, noise exposures of over 120 dBA can occur. Patients with claustrophobia or basic concerns about the magnetic resonance apparatus can be additionally frightened by loud examinations and/or unknown noises, such that an examination is possible only with the supplementation of calming agents, or is refused entirely.

SUMMARY OF THE INVENTION

An object of the invention is to provide a reduction and/or limitation and/or monitoring of the noise volume of a magnetic resonance apparatus.

The invention includes a method to control a magnetic resonance apparatus, wherein a noise volume-reduced operation mode of the magnetic resonance apparatus is activated depending on at least one predeterminable event.

A magnetic resonance apparatus can have multiple operating modes. An operating mode can include different settings of different components of the magnetic resonance apparatus. As used herein, a noise volume-reduced operating mode of the magnetic resonance apparatus means an operating model that includes a limitation and/or reduction and/or monitoring of the noise volume of the magnetic resonance apparatus. In this noise volume-reduced operating mode, the patient comfort and the willingness of a patient to cooperate can then be increased. Patients who are sensitive to noise can also be examined in this noise volume-reduced operating mode. The method can furthermore include that the noise volume-reduced operating mode of the magnetic resonance apparatus is deactivated again depending on at least one additional event. After the deactivation of the noise volume-reduced operating mode, the magnetic resonance apparatus can operate again in a standard operating mode in which the magnetic resonance apparatus operates with a noise volume that is typical for a magnetic resonance apparatus, for example.

The noise volume-reduced operating mode of the magnetic resonance apparatus can be activated when the at least one predeterminable event is triggered. A minimum, only one predeterminable event may lead to the activation of the noise volume-reduced operating mode, but it may also be the case that multiple predeterminable events, or one or multiple predeterminable events, occur so that the noise volume-reduced operating mode is activated. A predeterminable event is, for example, a fixed event. For example, such a predeterminable event may be an actuation of an input unit of the magnetic resonance apparatus by a user. The predeterminable event can be stored in an event database, and a regular check can be made as to whether a predeterminable event has been triggered (has occurred).

In an embodiment, the noise volume-reduced operating mode includes a limitation of the noise volume of the magnetic resonance apparatus. The noise volume-reduced operating mode can include a noise volume-limited operating mode and/or can consist solely of a noise volume-limited operating mode. As used herein, a limitation of the noise volume of the magnetic resonance apparatus is holding the noise volume of the magnetic resonance apparatus to or below a set limit. The set limit can be established in decibels (dB) and/or decibels (A) (dBA) and/or phone. The limitation of the noise volume of the magnetic resonance apparatus can be implemented such that defined settings of the magnetic resonance apparatus, which can lead to a higher noise volume than the set limit, cannot be selected. The noise volume-reduced operating mode can also include a monitoring of the limitation of the noise volume. It can therefore be ensured that the set limit of the noise volume is not exceeded with any selectable setting of the magnetic resonance apparatus. The limitation of the noise volume can have the advantage that hearing damage to the patient is avoided and/or that legal definitions are complied with and/or that the noise volume is perceived by a patient to be comfortable during the examination. As used herein, the noise volume of the magnetic resonance apparatus is the noise volume that is measured within the tunnel-like opening of the magnetic resonance apparatus in which a patient can be positioned. In particular, the relevant noise volume can be the noise volume that is measured at the level of a typical head position of a patient at a typical position in the magnetic resonance apparatus.

In an embodiment, the noise volume-reduced operating mode includes a limitation of the noise volume of the magnetic resonance apparatus to a maximum of 115 dBA. The noise volume-reduced operating mode advantageously includes a limitation of the noise volume of the magnetic resonance apparatus to a maximum of 110 dBA, advantageously to a maximum of 105 dBA, most advantageously to a maximum of 99 dBA. A limitation of the noise volume of the magnetic resonance apparatus to a maximum dBA value in particular means a limitation of the noise volume of the magnetic resonance apparatus with the maximum dBA value as a fixed limit. A limitation to a maximum of 99 dBA enables a patient examination without an obligation to protect hearing within the legal requirements of some countries. A limitation to a maximum of 99 dBA and a monitoring of the limitation of the noise volume ensures that a manufacturer of the magnetic resonance apparatus and/or a user of the magnetic resonance apparatus (a physician, for example) can examine patients without hearing protection without concerns of a claim that legally imposed requirements were not followed. A limitation of the noise volume of the magnetic resonance apparatus to even lower maximum dBA values (for example to 90 dBA or to 85 dBA or to 80 dBA) can be advantageous inasmuch as that the examination in the magnetic resonance apparatus is more comfortable for the patient with regard to the noise volume.

In a further embodiment the noise volume-reduced operating mode includes stopping data acquisition by the magnetic resonance apparatus upon exceeding the limitation of the noise volume of the magnetic resonance apparatus. The noise volume-reduced operating mode can thus include a stopping or a termination of a measurement of the magnetic resonance apparatus if a fixed noise volume limit in the magnetic resonance apparatus is exceeded. For example, if 99 dBA is exceeded in an examination of a patient without hearing protection, a measurement of the magnetic resonance apparatus can immediately be terminated. Exceeding the limitation of the noise volume of the magnetic resonance apparatus can be monitored by a noise volume measurement apparatus. The stopping of the measurement can be linked to additional conditions, for example whether the patient is wearing a hearing protection or not. Therefore it is ensured that the established noise volume limit is not exceeded during the measurement, or may possibly be exceeded only in a very short time period between exceeding the established noise volume limit and the termination of the measurement.

In another embodiment the noise volume-reduced operating mode includes monitoring of the noise volume of the magnetic resonance apparatus by a noise volume measurement device of the magnetic resonance apparatus. The noise volume of the magnetic resonance apparatus can be monitored continuously by the noise volume measurement device during the examination. The noise volume alternatively may be monitored only while the noise volume-reduced operating mode is activated. The noise volume measurement device measures the noise volume of the magnetic resonance apparatus. A dedicated noise volume measurement device (or noise measurement device) can be used to monitor the noise volume. The dedicated noise volume measurement device can be installed in the magnetic resonance apparatus. The additional use of a microphone that is already installed in the magnetic resonance apparatus for normal use for communication with the patient, for monitoring the noise volume, is advantageous. The noise volume measurement device can be positioned at the level of the head of a patient typically in the magnetic resonance apparatus. The noise volume measurement device can be calibrated by a noise with a fixed noise volume being generated in the magnetic resonance apparatus and measured by the noise volume measurement device in the magnetic resonance apparatus. The noise can include multiple frequencies. The noise can be similar to a magnetic resonance examination noise. The established noise volume can correspond to the limitation of the noise volume, for example a maximum of 99 dBA. The calibration of the noise volume measurement apparatus can be repeated at every service inspection of the scanner.

In a further embodiment, the noise volume-reduced operating mode includes a prevention of the selection capability and/or execution capability of defined imaging sequences and/or imaging protocols of the magnetic resonance apparatus. It is therefore ensured that the defined imaging sequences and/or imaging protocols are not executed and/or are not selected. For example, the prevention of the selection capability can be realized by covering the menu selection for the prevented protocol at the user interface with a grey overlay. Alternatively, a warning message and/or error message can appear on the user interface if an attempt is made to select the defined imaging sequences and/or imaging protocols.

In an embodiment the defined imaging sequences and/or imaging protocols is stored in a database. A negative list of all imaging sequences and/or imaging protocols that are prevented, or are prevented under certain conditions, can be stored in the database. Alternatively, a positive list can be stored in an additional or the same database, which positive list includes imaging sequences and/or imaging protocols which may continue to be selected and/or executed if the noise volume-limited operating mode is activated. The database can be stored centrally so that multiple magnetic resonance apparatuses have access to the database.

In another embodiment the defined imaging sequences and/or imaging protocols have a noise volume that is above a limitation of the noise volume of the magnetic resonance apparatus. The defined imaging sequences and/or imaging protocols can be selected such that an execution of the defined imaging sequences and/or imaging protocols by the magnetic resonance apparatus leads to a noise volume of the magnetic resonance apparatus beyond a limit of the noise volume. As soon as a noise volume beyond the limit or the established limit has been measured in the execution of an imaging sequence and/or an imaging protocol, this imaging sequence and/or this imaging protocol can be stored in the aforesaid database, possibly in the negative list. If this imaging sequence or imaging protocol is retrieved again, it can thus be prevented that the measurement is started again with this protocol. The imaging sequences and/or imaging protocols can also be selected according to their protocols with regard to the noise volume. If it is known that a defined parameter of an imaging sequence can lead to a noise volume above the set limit, the imaging sequence can be defined using this parameter and be stored in the database. The limitation of the noise volume can be fashioned as a fixed limit of the noise volume. The limitation of the noise volume can correspond to the limitation of the noise volume in the noise volume-limited operating mode, for example to a maximum of 99 dBA. The limitation of the noise volume can be higher or lower. As noted above, the noise volume is the noise volume within the tunnel-like opening of the magnetic resonance apparatus in which a patient can be positioned.

In an embodiment the noise volume-reduced operating mode includes a modification of at least one setting of a gradient system of the magnetic resonance apparatus. The gradient system can comprise gradient coils of the magnetic resonance apparatus. This is advantageous since it is primarily the switching process of the gradient fields that contributes to a high noise volume in the magnetic resonance apparatus. Therefore, the noise volume-reduced operating mode can include a modification of at least one setting that pertains to a switching process of a gradient system of the magnetic resonance apparatus. The settings of the gradient system can be modified such that the noise volume caused by the operation of the gradient system is limited. The modification of the settings of a gradient system can include a limitation of the settings of the gradient system.

In an embodiment the noise volume-reduced operating mode includes a limitation of the slew rate of the gradient system to an upper value. The slew rate of the gradient system is the rise rate and/or edge steepness and/or maximum rise or fall rate of the pulses produced by the gradient system. A high slew rate of the gradient system can be linked with a high noise volume caused by the gradient system. Therefore, a limitation of the slew rate leads to a limitation of the noise volume caused by the gradient system. The limitation of the slew rate to a possible maximum value of the slew rate can be implemented. This maximum value can be 75 mT/m/ms, advantageously 50 mT/m/ms, most advantageously 25 mT/m/ms.

In another embodiment the noise volume-reduced operating mode includes a cutout and/or deactivation of the helium pump of the magnet cooling system of a basic field magnet of the magnetic resonance apparatus. The magnet cooling, namely, the cooling of the basic field magnet of the magnetic resonance apparatus, generates a periodic noise that arises in the cryo head of the helium pump. Patients with claustrophobia or basic objections to the magnetic resonance apparatus can be additionally frightened by unfamiliar noises, such that an examination is only possible with the administration of calming agents or is refused altogether. If very quiet imaging sequences are executed in the magnetic resonance apparatus, the noise level in the examination room is defined by the magnet cooling of the magnetic resonance apparatus. Silence can then prevail in the examination room during the measurement due to the decrease and/or deactivation of the magnet cooling. The examination room then does not differ (with regard to the noise level) from other rooms of the hospital or practice. This leads to a calming of the patient and may remove the patient's fears of the magnetic resonance apparatus or of an examination in the magnetic resonance apparatus.

In another embodiment the noise volume-reduced operating mode includes a modification of the frequency of the cryo head of the helium pump. In particular, the frequency of the cryo head can be set to a value so that the periodic noise generated by the cryo head is comfortable for the patient. The frequency of the cryo head can be reduced, which leads to a reduction of the periodic noise.

In another embodiment the selection and/or the start of an imaging sequence of the magnetic resonance apparatus is registered, and the noise volume-reduced operating mode includes setting the frequency of the cryo head to a value that is sequence-specific to the imaging sequence. The selection and/or the start of the imaging sequence can be continuously monitored and/or detected during the activated, noise volume-reduced operating mode. In particular, the sequence-specific frequency of the cryo head can be a frequency that is matched to the noise of the imaging sequence. In particular, the sequence-specific frequency can be a frequency that is heard in the noise of the imaging sequence.

In another embodiment the selection and/or the start of an imaging sequence and/or of an imaging protocol of the magnetic resonance apparatus is registered, and the predeterminable event includes the selection and/or the start of defined imaging sequences and/or imaging protocols. This is particularly reasonable when the noise volume-reduced operating mode includes a deactivation and/or decrease of the magnet cooling and/or a variation of the frequency of the cryo head of the helium pump. The defined imaging sequences and/or imaging protocols that trigger the predeterminable event can then be very quiet imaging sequences and/or imaging protocols. The combination of the execution of a very quiet imaging sequence and/or a very quiet imaging protocol and the deactivated and/or decreased magnet cooling and/or the modified frequency of the cryo head of the helium pump then leads to a very quiet noise volume in the examination room. This can be very comfortable for a patient and can remove the patient's fear of the examination in the magnetic resonance apparatus. The fact that the predeterminable event includes a defined condition and/or a defined other event can mean that the predeterminable event is triggered by the defined condition and/or the defined other event.

One embodiment provides that the predeterminable event includes an operation of an input unit of the magnetic resonance apparatus by a user. The operation of the input unit can include the operation of a switch. The operation of the input unit can also include at least one input in an input console by means of an input device. The switch and/or the input console can be part of the input unit of the magnetic resonance apparatus. The operation of the input unit enables a user to activate (and/or possibly deactivate again) the noise volume-reduced operating mode of the magnetic resonance apparatus. The user can thus activate the noise volume-reduced operating mode before a patient enters the examination room and/or before the examination of the patient in the magnetic resonance apparatus begins.

In another embodiment the predeterminable event includes setting a defined registration parameter of a patient in a defined registration parameter range during the registration of the patient. During the registration of a patient, defined information about a patient is recorded. The registration of the patient typically occurs before the examination of the patient in the magnetic resonance apparatus. The information about the patient includes registration parameters, for example the age, name, height and weight of the patient. A particularly relevant registration parameter for defining the predeterminable event in accordance with the invention is the age of the patient. The predeterminable event can be triggered (and thus the noise volume-reduced operating mode of the magnetic resonance apparatus can be activated) when an age which is above and/or below at least one defined limit is set in the registration of a patient. Younger patients are often more noise-sensitive, such that an activation of a noise volume-reduced operating mode for this patient can be more comfortable and safer. The predeterminable event can be triggered automatically if a patient is registered with a registration parameter in a defined registration parameter range. During and/or after the registration, it can also be suggested to a user (possibly depending on a defined registration parameter of the registration) to trigger the predeterminable event, and thus to activate the noise volume-reduced operating mode of the magnetic resonance apparatus.

In another embodiment the activation state of the noise volume-reduced operating mode is detected and displayed at an output unit of the magnetic resonance apparatus. The activation state of the noise volume-reduced operating mode can include two states, namely the activated state and the deactivated state. The activation state of the noise volume-reduced operating mode can be indicated as a symbol on an output unit. It can also be indicated by lighting a (possibly colored) illumination device.

The control device according to the invention for a magnetic resonance apparatus is designed to execute a method according to the invention. For this purpose, the control device has control components that are necessary and/or advantageous for execution of the method according to the invention as discussed above. The control device can be designed to send control signals to the magnetic resonance apparatus and/or to receive and/or process control signals in order to execute the method according to the invention. The control device thus serves to efficiently execute a method according to the invention. For this purpose, computer programs and additional software can be stored on a memory unit of the control device that cause a processor of the control device to automatically control and/or execute the method workflow of a method according to the invention. The control device activates a noise volume-reduced operating mode of the magnetic resonance apparatus that increases the patient comfort and the willingness of the patient to cooperate. Noise-sensitive patients can also be examined in this noise volume-reduced operating mode.

The magnetic resonance apparatus according to the invention has a control device according to the invention. The control device can be integrated into the magnetic resonance apparatus. The control device can also be installed separately from the magnetic resonance apparatus. The control device can be connected with the magnetic resonance apparatus. The magnetic resonance apparatus, with the control device according to the invention, executes the method according to the invention. The noise volume of the magnetic resonance apparatus can therefore be reduced and/or monitored and/or limited. In a noise volume-reduced operating mode of the magnetic resonance apparatus, the patient comfort and the willingness of the patient to cooperate can then be increased. Noise-sensitive patients can also be examined in this noise volume-reduced operating mode.

The invention also encompasses a non-transitory, computer-readable data storage medium encoded with programming instructions that, when the storage medium is loaded into a control device, namely a processor thereof, cause the control device or processor to implement one or more of the embodiments of the method as described above. For this purpose, the control device or processor may include auxiliary components such as a working memory, a graphic card, and/or a logic unit.

Examples of electronically readable data storage media are a DVD, a magnetic tape or a USB stick on which is stored electronically readable control information.

DESCRIPTION OF THE PREFERRED EMBODIMENTS

Figure 1:
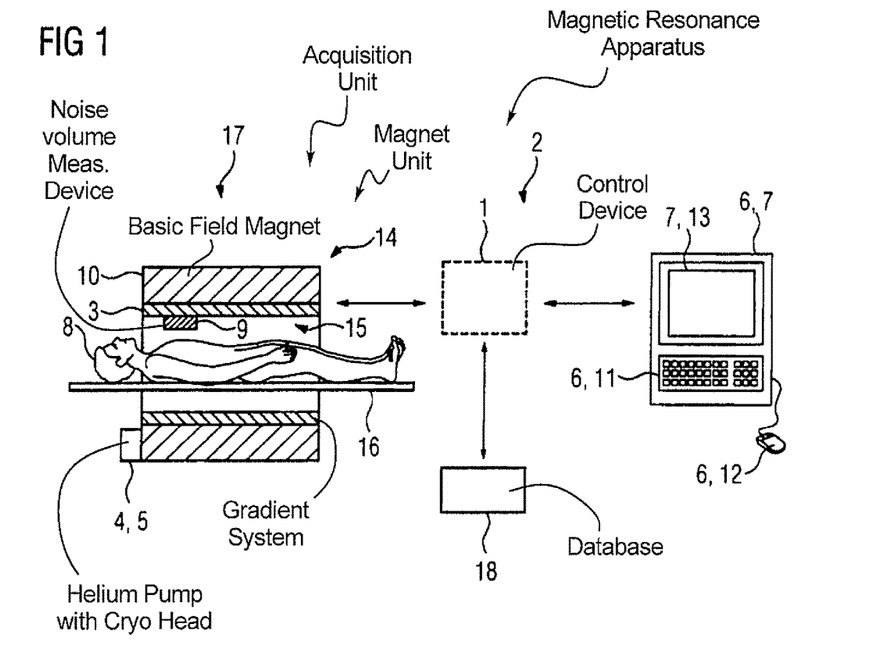
FIG. 1 schematically illustrates a magnetic resonance apparatus designed to execute a method according to the invention.

FIG. 1 shows a magnetic resonance apparatus 2 designed to execute a method according to the invention, in a schematic presentation. The magnetic resonance apparatus 2 has an acquisition unit 17 that includes a magnet unit 14 and a patient receptacle region 15, surrounded by the magnet unit 14, to accommodate a patient 8, wherein the patient receptacle region 15 is cylindrically surrounded by the magnet unit 14 in a circumferential direction. The patient 8 can be slid into a patient receptacle region 15 by means of a patient bearing device 16 of the magnetic resonance apparatus 2. For this, the patient bearing device 16 is arranged so as to be movable within the patient receptacle region 15.

The magnet unit 14 has a basic field magnet 10 that is designed to generate a strong—and in particular constant—basic magnetic field in the operation of the magnetic resonance apparatus 2. The magnet unit 14 furthermore has a gradient system 3 to generate magnetic field gradients, which is used for a spatial coding during an imaging.

Furthermore, the magnet unit 14 has a helium pump 4 that has a cryo head 5. The helium pump 4 is integrated into the magnet cooling of the basic field magnet 10. Furthermore, the magnetic resonance apparatus 2 has a noise volume measurement device 9. In the shown case, this is positioned within the patient receptacle region 15 and designed as a microphone integrated into the acquisition unit 17, which microphone is normally used for communication with the patient. An embodiment of the noise volume measurement device 9 as a separately positioned measurement device, advantageously within the patient receptacle region 15, would also be conceivable. Furthermore, the magnetic resonance apparatus 2 has an output unit 7 which is designed as a monitor 13. The magnetic resonance apparatus 2 also has an input unit 6 which is designed as a keyboard 11 and mouse 12.

To control the magnetic resonance apparatus 2, the magnetic resonance apparatus 2 has a control device 1. This is designed to send control signals to the acquisition unit 17 and to the output unit 7 of the magnetic resonance apparatus 2. the control device 1 is furthermore designed to receive control signals from the input unit 6 and the acquisition unit 17. The control device 1 can furthermore access a database 18 or retrieve information from a database 18.

The depicted magnetic resonance apparatus 2 can naturally include additional components that magnetic resonance apparatuses 2 conventionally have. A general functionality of a magnetic resonance apparatus 2 is additionally known to the person skilled in the art, such that a more detailed description of the general components is omitted.

Figure 2:
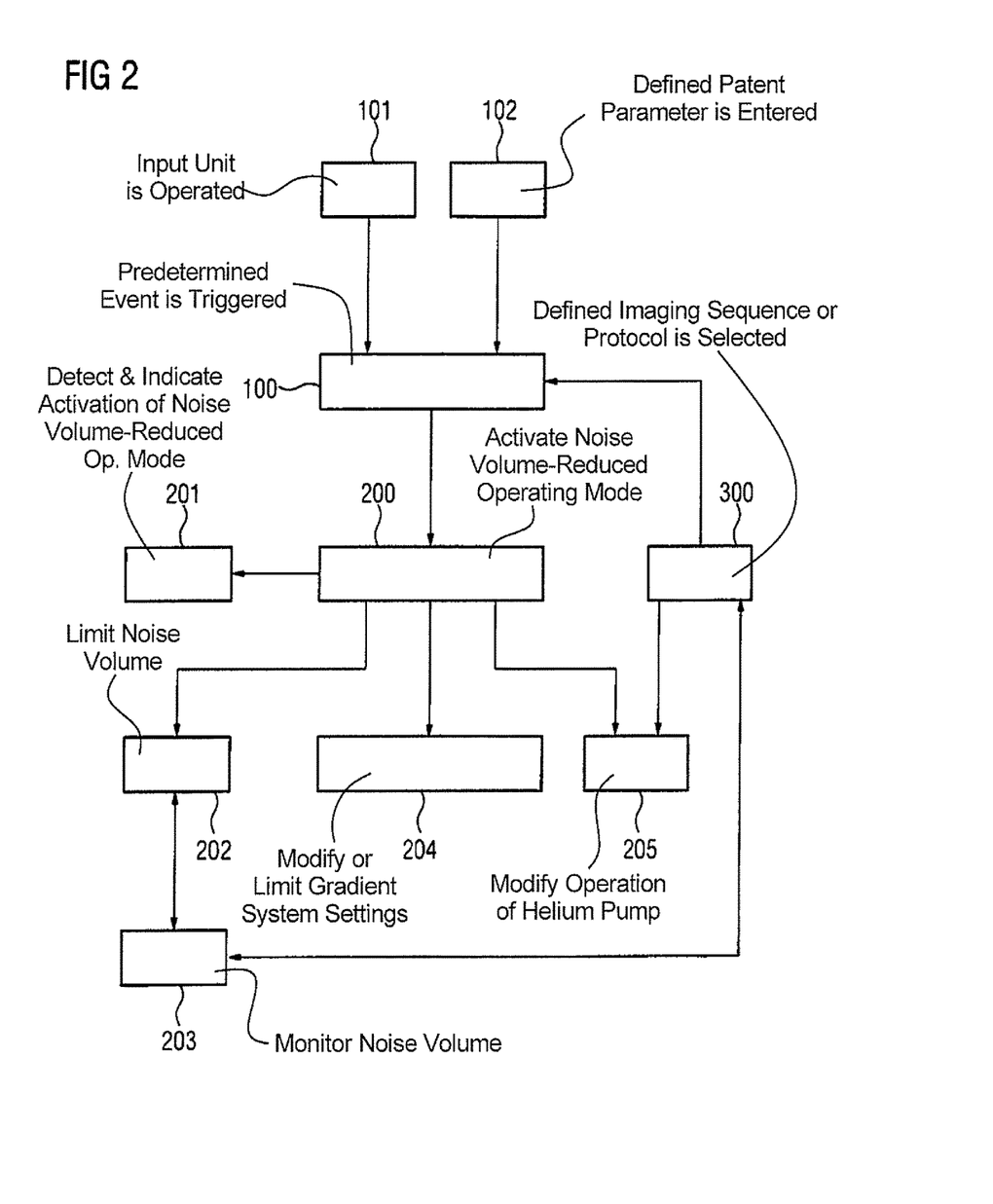
FIG. 2 is a flowchart of an embodiment of the method according to the invention to control a magnetic resonance apparatus.

In particular, the control device 1 is designed to execute a method according to the invention as depicted in FIG. 2, wherein a noise volume-reduced operating mode of the magnetic resonance apparatus 2 is activated depending on at least one predeterminable event. In a first method step 100, the predetermined event occurs. In a further method step 200, the noise volume-reduced operating mode of the magnetic resonance apparatus is thereupon activated.

The predeterminable event is triggered if the input unit 6 of the magnetic resonance apparatus 2 is operated by a user in a further method step 101; and/or if an adjustment of a defined registration parameter of a patient 8 in a defined parameter range is made during the registration in a further method step 102; and/or if a selection and/or start of a defined imaging sequence and/or of a defined imaging protocol of the magnetic resonance apparatus 2 is detected in a further method step 300. Only one of the three method steps 101, 102, 300 can lead to the triggering of the predeterminable event. Alternatively, a combination of multiple method steps 101, 102, 300 can also be necessary so that the predeterminable event is triggered.

In a further method step 201, the activation state of the noise volume-reduced operating mode is detected and indicated at the output unit 7 of the magnetic resonance apparatus 2. The activation of the noise volume-reduced operating mode can lead to different events which are encompassed by the noise volume-reduced operating mode. In a further method step 202, a limitation of the noise volume of the magnetic resonance apparatus 2 can thus take place. This limitation of the noise volume of the magnetic resonance apparatus 2 can be monitored in a further method step 203. The limitation of the noise value to a fixed maximum dBA value (for example to 99 dBA) can take place. The monitoring of the limitation of the noise volume can lead to a termination of a measurement of the magnetic resonance apparatus 2. The control device 1 can receive signals from the noise volume measurement device 9 and stop a measurement via the acquisition unit 17 based on the measured noise volume.

To monitor the limitation of the noise volume, it can be necessary that it be detected by the magnetic resonance apparatus 2 in the aforesaid method step 300 whether a defined imaging sequence and/or a defined imaging protocol have presently been selected and/or started. For this, an important signal path leads from the acquisition unit 17 and/or from the input unit 6 to the control device 1. The signal path includes information as to which imaging sequences and/or imaging protocols are presently selected and/or executed by the magnetic resonance apparatus 2. The implementation and/or the selection of defined imaging sequences and/or defined imaging protocols can be prevented and/or lead to a termination of the measurement. For this, the control device 1 can access a database 18 in which the defined imaging sequences and/or defined imaging protocols are stored, the execution of which is prevented in a noise volume-reduced operating mode of the magnetic resonance apparatus 2. The control device 1 can also actively store the defined imaging sequences and/or defined imaging protocols in the database 18 if, for example, it the control device 1 has detected that the execution of the defined imaging sequences and/or defined imaging protocols leads to a noise volume in the magnetic resonance apparatus 2 beyond a certain limit.

Furthermore, a modification and/or limitation of the settings of a gradient system 3—in particular a limitation of the slew rate of the gradient system 3—can take place in a further method step 204 after activation of the noise volume-reduced operating mode. For this purpose, the control device 1 can send control signals to the gradient system 3, and thus modify and/or limit settings of the gradient system 3.

Furthermore, after activation of the noise volume-reduced operating mode, a modification of the function of the helium pump 4 of the magnet cooling of the basic field magnet 10 of the magnetic resonance apparatus 2 can take place in a further method step 205. The modification of the function of the helium pump 4 can include a cutoff and/or deactivation of the helium pump 4. For this, the control device can send signals to the helium pump 4 and/or the cryo head 5 of the helium pump 4. Alternatively, the modification of the function of the helium pump 4 can include a modification of the frequency of the cryo head 5 of the helium pump 4 to a value which is sequence-specific to a defined imaging sequence and/or a defined imaging protocol. For this, it can again be necessary that, in the aforesaid method step 300, it is detected whether a defined imaging sequence and/or a defined imaging protocol has presently been selected and/or started.

The method steps 100-300 of the method according to the invention are executed by the control unit 1 together with the magnetic resonance apparatus 2. For this, the control unit 1 comprises a software and/or computer programs required for this that are stored in a memory unit of the control unit 1. The software and/or computer programs include program means that are designed to execute the method according to the invention if said computer program and/or the software is executed in the control unit 1 by means of a processor unit of the magnetic resonance apparatus 2.

In summary, the invention concerns a method to control a magnetic resonance apparatus; a control device; a magnetic resonance apparatus; a computer program product; and an electronically readable data medium. So that a reduction and/or limitation and/or monitoring of the noise volume of a magnetic resonance apparatus is enabled, it is proposed that a noise volume-reduced operating mode of the magnetic resonance apparatus is activated depending on at least one predeterminable event.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to operate a magnetic resonance (MR) apparatus having an MR data acquisition unit comprising gradient coils, said method comprising:

in a control computer, generating control signals and supplying said control signals to said MR data acquisition unit in order to operate said MR data acquisition unit so as to execute an MR data acquisition procedure, said control signals including signals that cause switching of currents in said gradient coils that produces a level of audible noise during said data acquisition procedure;

upon detection of a predetermined event by said control computer during said data acquisition procedure, changing operation of said MR data acquisition unit from said control computer into a noise volume-reduced operating mode by altering at least one of said control signals generated in said control computer in a manner that reduces said level of audible noise, and supplying said at least one altered control signal from said control computer to said MR data acquisition unit; and at said control unit, making a plurality of operating protocols available for selection of a user, to operate said data acquisition unit with a selected one of said protocols, each of said protocols causing control signals respectively associated therewith to be provided from said control unit to said data acquisition unit, and comprising altering said control signals by, in said control unit, automatically preventing selection or execution of at least one of said protocols upon detection of said at least one predetermined event.

2. A method as claimed in claim 1 comprising detecting said predetermined event by monitoring said level of audible noise of said data acquisition unit with a noise volume measurement device in said data acquisition unit, and providing a noise volume measurement signal, representing said level of audible noise of said data acquisition unit, from said noise volume measurement device to said control unit.

3. A method as claimed in claim 1 comprising storing said protocols in a memory accessible by said control unit.

4. A method as claimed in claim 3 comprising storing said protocols in said memory with a designation associated with each protocol that designates the respective protocol with regard to acceptability for use in said noise volume-reduced operating mode.

5. A method as claimed in claim 1 comprising detecting a selection or start of an imaging sequence, or selection of an imaging protocol, as said at least one predetermined event.

6. A method as claimed in claim 1 wherein said control unit comprises a user interface, and comprising detecting said at least one predetermined event as operation of said interface by a user.

7. A method as claimed in claim 1 wherein said control unit is in communication with a display unit, and comprising displaying an indication, from said control unit, at said display unit indicating an activated state of said noise volume-reduced operating mode.

8. A control computer for operating a magnetic resonance (MR) apparatus comprising an MR data acquisition unit comprising gradient coils, said control computer comprising:
an input interface and an output interface;
a processor in communication with said input interface and said output interface;
said processor being configured to generate control signals and to supply said control signals via said output interface to said MR data acquisition unit in order to operate said MR data acquisition unit so as to execute an MR data acquisition procedure, said control signals including signals that cause switching of currents in said gradient coils that produces a level of audible noise during said data acquisition procedure;
upon detection of a predetermined event via said input interface during said data acquisition procedure, said processor being configured to change operation of said MR data acquisition unit from said control computer into a noise volume-reduced operating mode by altering at least one of said control signals generated in said processor in a manner that reduces said level of audible noise, and to supply said at least one altered control signal from said processor via said output interface to said MR data acquisition unit; and
said processor being configured to make a plurality of operating protocols available for selection of a user, to operate said data acquisition unit with a selected one of said protocols, each of said protocols causing control signals respectively associated therewith to be provided from said control unit to said data acquisition unit, and said processor being configured to alter said control signals automatically preventing selection or execution of at least one of said protocols upon detection of said at least one predetermined event.

9. A method to operate a magnetic resonance (MR) apparatus having an MR data acquisition unit comprising gradient coils, said method comprising:
in a control computer, generating control signals and supplying said control signals to said MR data acquisition unit in order to operate said MR data acquisition unit so as to execute an MR data acquisition procedure, said control signals including signals that cause switching of currents in said gradient coils that produces a level of audible noise during said data acquisition procedure; and
upon detection of a predetermined event by said control computer during said data acquisition procedure, changing operation of said MR data acquisition unit from said control computer into a noise volume-reduced operating mode by altering at least one of said control signals generated in said control computer in order to limit a slew rate when switching said currents in said gradient coils so as to reduce said level of audible noise, and supplying said at least one altered control signal from said control computer to said MR data acquisition unit.

10. A method to operate a magnetic resonance (MR) apparatus having an MR data acquisition unit comprising gradient coils, and a control unit comprising a user interface, said method comprising:
in said control computer, generating control signals and supplying said control signals to said MR data acquisition unit in order to operate said MR data acquisition unit so as to execute an MR data acquisition procedure, said control signals including signals that cause switching of currents in said gradient coils that produces a level of audible noise during said data acquisition procedure;
upon detection of a predetermined event by said control computer during said data acquisition procedure, changing operation of said MR data acquisition unit from said control computer into a noise volume-reduced operating mode by altering at least one of said control signals generated in said control computer in a manner that reduces said level of audible noise, and supplying said at least one altered control signal from said control computer to said MR data acquisition unit; and
via said user interface, receiving an entry made by a user of patient-specific operating parameters for operating said MR data acquisition unit, and detecting, as said at least one predetermined event, entry of a predetermined patient-specific parameter via said interface.

11. A control computer for operating a magnetic resonance (MR) apparatus comprising an MR data acquisition unit comprising gradient coils, said control computer comprising:
an input interface and an output interface;
a processor in communication with said input interface and said output interface;
said processor being configured to generate control signals and to supply said control signals via said output interface to said MR data acquisition unit in order to operate said MR data acquisition unit so as to execute an MR data acquisition procedure, said control signals including signals that cause switching of currents in said gradient coils that produces a level of audible noise during said data acquisition procedure; and
upon detection of a predetermined event via said input interface during said data acquisition procedure, said processor being configured to change operation of said MR data acquisition unit from said control computer into a noise volume-reduced operating mode by altering at least one of said control signals generated in said processor in order to limit a slew rate when switching said currents in said gradient coils so as to reduce said level of audible noise, and to supply said at least one altered control signal from said processor via said output interface to said MR data acquisition unit.

12. A control computer for operating a magnetic resonance (MR) apparatus comprising an MR data acquisition unit comprising gradient coils, said control computer comprising:
an input interface and an output interface;
a processor in communication with said input interface and said output interface;
said processor being configured to generate control signals and to supply said control signals via said output interface to said MR data acquisition unit in order to operate said MR data acquisition unit so as to execute an MR data acquisition procedure, said control signals including signals that cause switching of currents in said gradient coils that produces a level of audible noise during said data acquisition procedure;
upon detection of a predetermined event via said input interface during said data acquisition procedure, said processor being configured to change operation of said MR data acquisition unit from said control computer into a noise volume-reduced operating mode by altering at least one of said control signals generated in said processor in a manner that reduces said level of audible noise, and to supply said at least one altered control signal from said processor via said output interface to said MR data acquisition unit; and said processor being configured to receive entry by a user, via said input interface, of patient-specific operating parameters for operating said MR data acquisition unit, and wherein said processor is configured to detect, as said at least one predetermined event, entry of a predetermined patient-specific parameter via said input interface.

* * * * *